US012797562B2

(12) United States Patent
Fato et al.

(10) Patent No.: US 12,797,562 B2
(45) Date of Patent: Nov. 17, 2026

(54) DRY POWDER INHALER FOR PULMONARY OR NASAL DELIVERY

(71) Applicant: AMIKO S.R.L., Milan (IT)

(72) Inventors: Alessandro Fato, Milan (IT); Federico Martijn Grinovero, Vermezzo con Zelo (IT)

(73) Assignee: AMIKO S.R.L., Milan (IT)

( * ) Notice: Subject to any disclaimer, the term of this patent is extended or adjusted under 35 U.S.C. 154(b) by 932 days.

(21) Appl. No.: 17/641,966

(22) PCT Filed: Sep. 28, 2020

(86) PCT No.: PCT/IB2020/059039
§ 371 (c)(1),
(2) Date: Mar. 10, 2022

(87) PCT Pub. No.: WO2021/059249
PCT Pub. Date: Apr. 1, 2021

(65) Prior Publication Data

US 2022/0305220 A1 Sep. 29, 2022

(30) Foreign Application Priority Data

Sep. 27, 2019 (IT) ........................ 102019000017417

(51) Int. Cl.
*A61M 15/00* (2006.01)
*A61B 5/087* (2006.01)
(Continued)

(52) U.S. Cl.
CPC ......... *A61M 15/0028* (2013.01); *A61B 5/087* (2013.01); *A61B 5/091* (2013.01);
(Continued)

(58) Field of Classification Search
CPC ................ A61M 15/00; A61M 15/001; A61M 15/0005; A61M 15/0006; A61M 15/0008;
(Continued)

(56) References Cited

U.S. PATENT DOCUMENTS 6,230,707 B1 * 5/2001 Horlin ............... A61M 15/0028
128/203.15
11,058,833 B2 * 7/2021 Holtz .................. A61M 15/008
(Continued)

FOREIGN PATENT DOCUMENTS

CN 103442758 A 12/2013
CN 107614038 A 1/2018
(Continued)

*Primary Examiner* — Colin W Stuart
(74) *Attorney, Agent, or Firm* — Dickinson Wright PLLC; Andrew D. Dorisio; Nicholas P. Coleman

(57) ABSTRACT

A dry powder inhaler has a chamber for housing a capsule and an inhalation channel, the chamber is shaped in order to determine an agitated motion of the capsule in the chamber during an inhalation of a user, the inhaler includes a capsule-piercing mechanism arranged to pierce a capsule in the chamber and a monitoring system including an accelerometer arranged on a printed circuit board in order to measure mechanical oscillations determined at least by the agitated motion and by a flow of air through the chamber and/or inhalation channel; a detection unit arranged to detect an activation of the capsule-piercing mechanism; and an electronic processing unit configured to receive signals from the detection unit and from the accelerometer. Reception of a signal from the detection unit triggers processing of signals from the accelerometer by the electronic processing unit in order to generate inhalation data.

19 Claims, 12 Drawing Sheets

(51) Int. Cl.
*A61B 5/091* (2006.01)
*A61M 11/00* (2006.01)

(52) U.S. Cl.
CPC ...... *A61M 11/003* (2014.02); *A61M 15/0008* (2014.02); *A61M 15/0025* (2014.02); *A61M 15/0035* (2014.02); *A61B 2562/0219* (2013.01); *A61M 2202/064* (2013.01); *A61M 2205/3592* (2013.01); *A61M 2205/8206* (2013.01); *A61M 2207/00* (2013.01)

(58) Field of Classification Search
CPC .......... A61M 15/0021; A61M 15/0026; A61M 15/0028; A61M 15/003; A61M 15/0033; A61M 15/0065; A61M 15/0068; A61M 15/008; A61M 15/0086; A61M 2202/064; A61M 2205/33; A61M 2205/3306; A61M 2205/3317; A61M 2205/3327; A61M 2205/3375; A61M 2205/35; A61M 2205/3515; A61M 2205/60; A61M 2205/6036; A61M 2205/6045; A61M 2205/6054; A61M 2205/6063
See application file for complete search history.

(56) References Cited

U.S. PATENT DOCUMENTS

2003/0000523 A1* 1/2003 Citterio ............ A61M 15/0033 128/203.15
2009/0308387 A1* 12/2009 Andersen ............ A61M 15/00 128/203.15
2015/0100335 A1* 4/2015 Englehard ........... A61M 15/008 705/2
2016/0129182 A1* 5/2016 Schuster ............ A61M 15/008 702/56
2017/0290527 A1* 10/2017 Morrison ............ A61B 5/4833
2018/0264207 A1 9/2018 Von Hollen et al.
2018/0369513 A1 12/2018 Hannon et al.
2019/0385727 A1* 12/2019 Manice ............ A61M 15/0083
2020/0330719 A1* 10/2020 Segal ............ A61M 15/008
2020/0345588 A1* 11/2020 Merrell ............ A61M 15/009
2021/0008304 A1* 1/2021 Marcoz ............ A61M 15/0083
2021/0085564 A1* 3/2021 Beyleveld ............ A61B 5/0022

FOREIGN PATENT DOCUMENTS

WO 2016116591 A1 7/2016
WO 2017199215 A1 11/2017
WO 2018160073 A1 9/2018

* cited by examiner

DRY POWDER INHALER FOR PULMONARY OR NASAL DELIVERY

TECHNICAL FIELD

The subject-matter disclosed herein relates to a dry powder inhaler, in particular capsule based refillable single-dose dry powder inhaler for pulmonary or nasal delivery. The subject-matter disclosed herein further relates to an inhalation kit for pulmonary or nasal delivery.

BACKGROUND ART

Known capsule-based inhalers, such as the RS01 model disclosed in document EP 1270034, are configured to be loaded with a dose of medication in the form of a capsule.

Such inhalers are provided with needles or other sharp parts pointing towards the capsule and arranged to be actuated by the user in order to tear the outer shell of the capsule.

During inhalation, the turbulent flow of air causes the capsule to spin and release the powder to be inhaled by the user.

These models of inhalers allow the gradual release and delivery of a precise dose of medication to the patient with a wide range of capsule materials and powder formulation.

Current clinical evidence suggests that inhaled therapy often fails to achieve expected results due to low adherence and poor inhalation technique by the patient.

There have been attempts at addressing these problems with inhalers combined with monitoring devices, however these attempts have led to unsatisfactory results due to poor or limited monitoring performance, or high vulnerability of the monitoring devices to mechanical shocks, or their susceptibility to factors external to the interaction between inhaler and user which generates signal disturbances and errors, or their impact on drug delivery performance, or their excessive cost. Thus, there is a general need for monitoring simply and reliably an inhaler, in particular its usage, and generating and providing inhalation data.

SUMMARY

It is the object of the subject-matter disclosed herein to improve the known dry powder inhalers in one or more ways.

According to one aspect, the subject-matter disclosed herein relates to a dry powder inhaler for pulmonary or nasal delivery, having a chamber for housing therein a capsule containing a dry powder formulation and an inhalation channel in fluid communication with said chamber, said chamber being shaped in order to determine an agitated motion of said capsule in said chamber during an inhalation of a user through said inhalation channel, said inhaler comprising:

a capsule-piercing mechanism arranged to pierce said capsule in said chamber; and a monitoring system comprising:

an accelerometer arranged to measure mechanical oscillations determined at least by said agitated motion and by a flow of air through said chamber and/or inhalation channel;

a detection unit arranged to detect an activation of the capsule-piercing mechanism; and an electronic processing unit configured to receive signals from said detection unit and from said accelerometer, wherein reception of a signal from said detection unit triggers processing of signals from said accelerometer by said electronic processing unit in order to generate inhalation data, wherein said monitoring system comprises a printed circuit board mechanically coupled to said inhaler body in order to be affected by mechanical oscillations during said inhalation, wherein said accelerometer is fixed on said printed circuit board (48) in order to measure said mechanical oscillations, and wherein said printed circuit board is arranged to transmit the mechanical oscillations from the inhaler body to the accelerometer.

According to another aspect, the subject-matter disclosed herein relates to a dry powder inhalation kit for pulmonary or nasal delivery, comprising:

an inhaler body;

a mouthpiece detachably connectable to said inhaler body;

a monitoring module detachably connectable to the inhaler body, said inhaler body and said mouthpiece defining, when connected, a chamber for housing therein a capsule containing a dry powder formulation and an inhalation channel in fluid communication with said chamber, said chamber being shaped in order to determine an agitated motion of said capsule in said chamber during an inhalation of a user through said inhalation channel; and a capsule-piercing mechanism arranged on said inhaler body to pierce said capsule in said chamber;

said monitoring module integrating a monitoring system comprising:

an accelerometer arranged on a printed circuit board in order to measure mechanical oscillations determined at least by said agitated motion and by a flow of air through said chamber and/or inhalation channel;

a detection unit arranged to detect an activation of the capsule-piercing mechanism; and an electronic processing unit configured to receive signals from said detection unit and from said accelerometer, wherein reception of a signal from said detection unit triggers processing of signals from said accelerometer by said electronic processing unit in order to generate inhalation data.

Despite common confusion, acceleration sensors and acoustic sensors differ quite significantly. Accelerometers respond to accelerations, whereas microphones respond to pressure variations resulting from particles vibrating in the air and gas pressure waves in the air.

There are prior-art solutions that use an acoustic sensor to monitor sound pressure indicative of an inhalation. A solution of this type is known from e.g. WO 2018/160073 A1.

Such prior-art solutions are prone to suffer from signal disturbances, interference and errors caused by ambient noise sources present in the environment where the inhaler is used and monitored.

BRIEF DESCRIPTION OF THE DRAWINGS

A more complete appreciation of the disclosed embodiments of the invention and many of the attendant advantages thereof will be readily obtained as the same becomes better understood by reference to the following detailed description when considered in connection with the accompanying drawings, wherein.

DETAILED DESCRIPTION OF EMBODIMENTS

Figure 1:
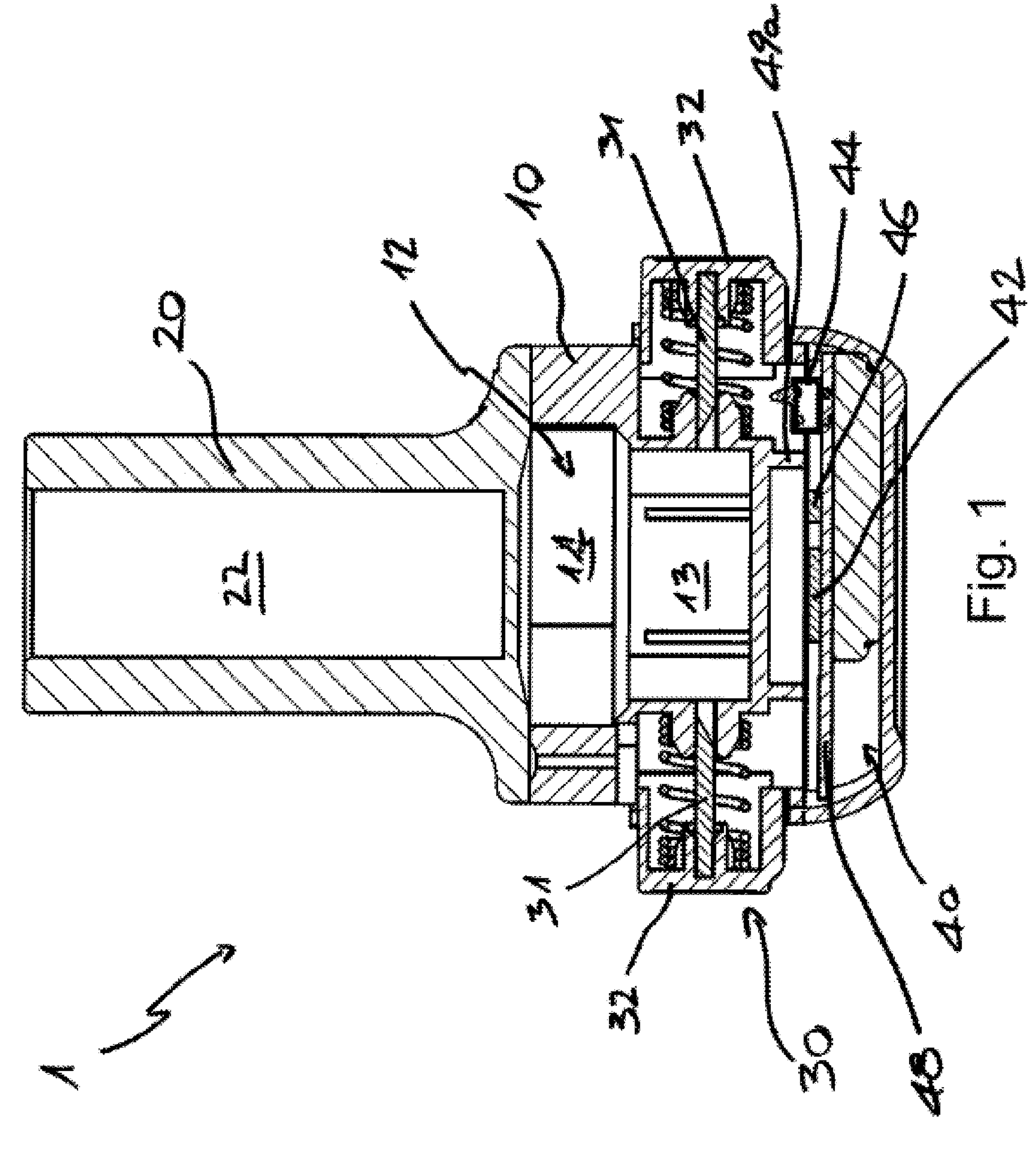
FIG. 1 illustrates a section view of an embodiment of an inhaler as disclosed herein.

Reference now will be made in detail to embodiments of the disclosure, one or more examples of which are illustrated in the drawings. Each example is provided by way of explanation of the disclosure, not limitation of the disclosure. In fact, it will be apparent to those skilled in the art that various modifications and variations can be made in the present disclosure without departing from the scope or spirit of the disclosure. Reference throughout the specification to "one embodiment" or "an embodiment" or "some embodiments" means that the particular feature, structure or characteristic described in connection with an embodiment is included in at least one embodiment of the subject matter disclosed. Thus, the appearance of the phrase "in one embodiment" or "in an embodiment" or "in some embodiments" in various places throughout the specification is not necessarily referring to the same embodiment(s). Further, the particular features, structures or characteristics may be combined in any suitable manner in one or more embodiments.

When introducing elements of various embodiments the articles "a", "an", "the", and "said" are intended to mean that there are one or more of the elements. The terms "comprising", "including", and "having" are intended to be inclusive and mean that there may be additional elements other than the listed elements.

According to one aspect and with reference to the enclosed figures, the subject-matter disclosed herein provides for a dry powder inhaler for pulmonary or nasal delivery; an embodiment thereof is indicated with reference number 1 and referred to as "inhaler 1" in the following.

The powder inhaler (labeled 1 in the figures) has an inhaler body (labeled 10 in the figures) and a mouthpiece (labeled 20 in the figures). The inhaler body defines a chamber (labeled 12 in the figures) for housing a capsule containing a dose of powder formulation.

Figure 9:
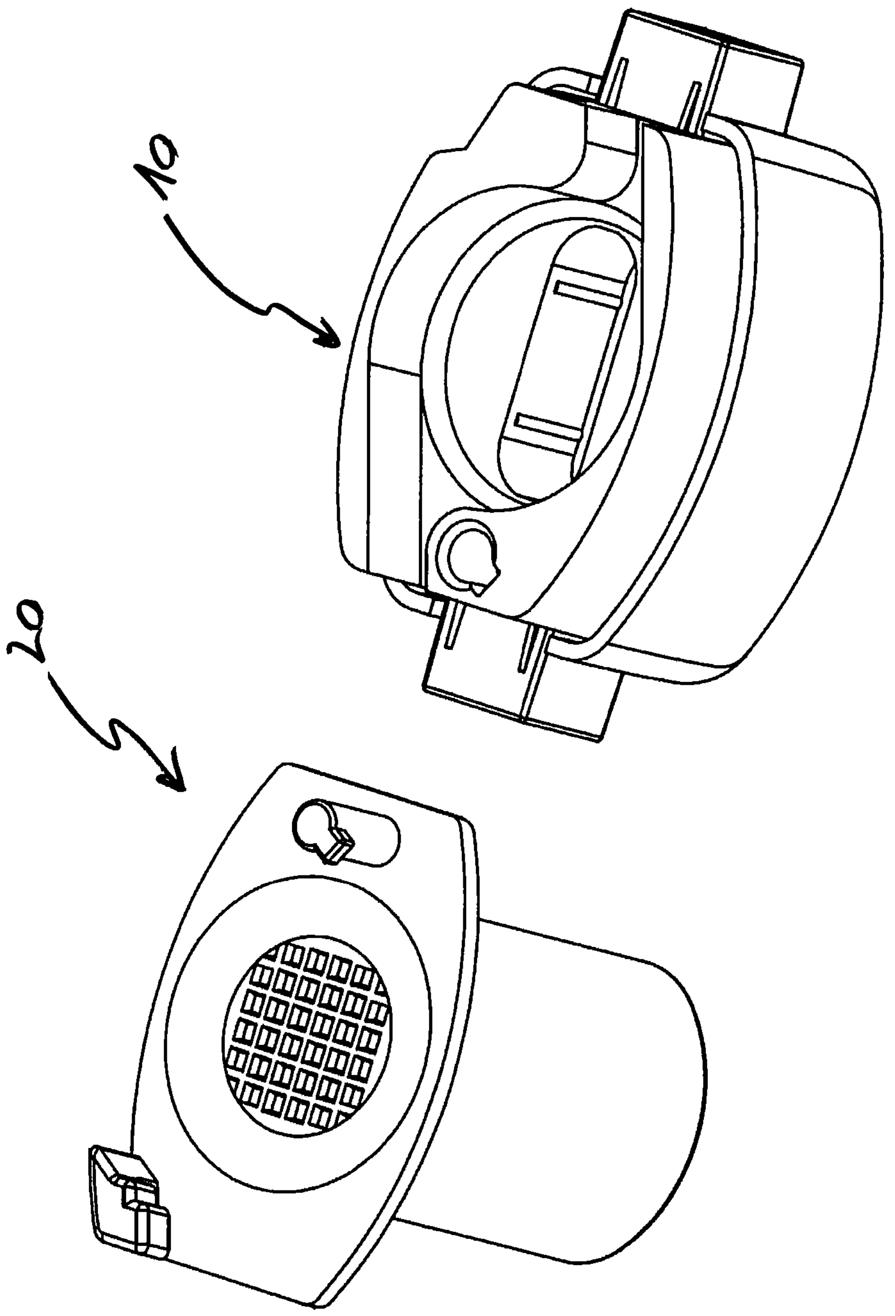
FIG. 9 illustrates a prospective view of an embodiment of an inhaler as disclosed herein.
Figure 10:
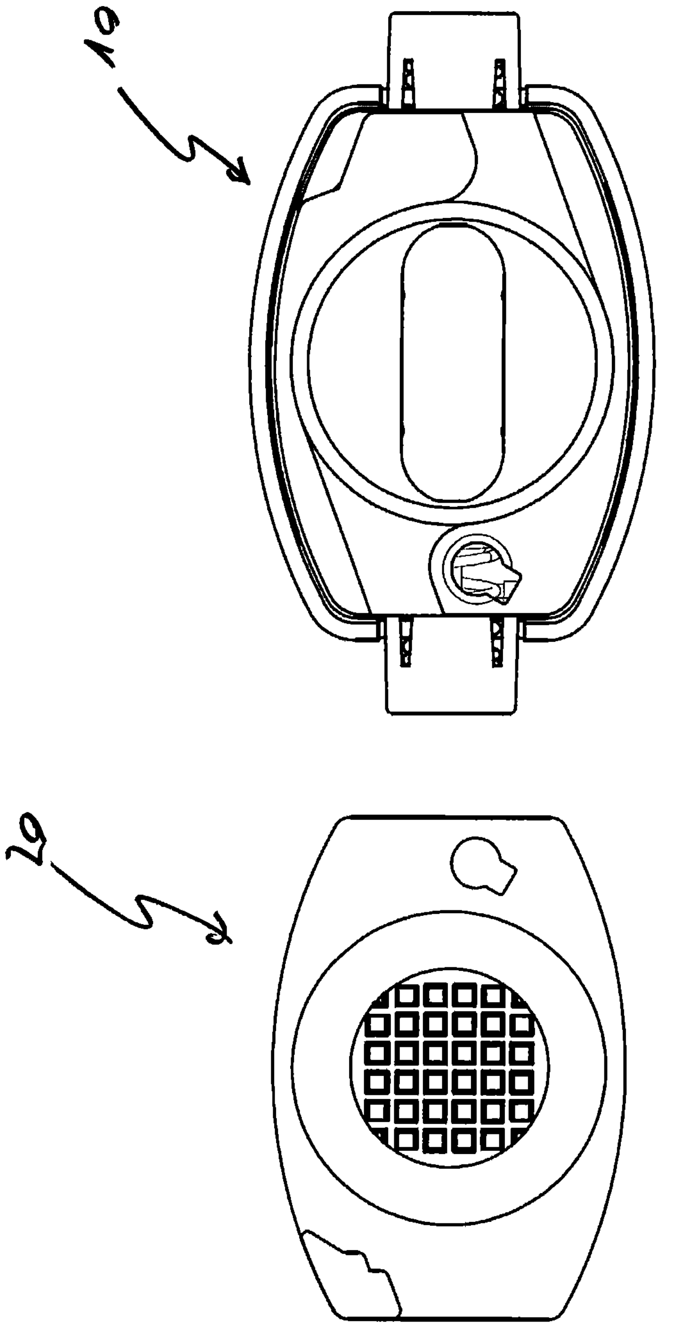
FIG. 10 illustrates a top view of the inhaler of FIG. 9.
Figure 11:
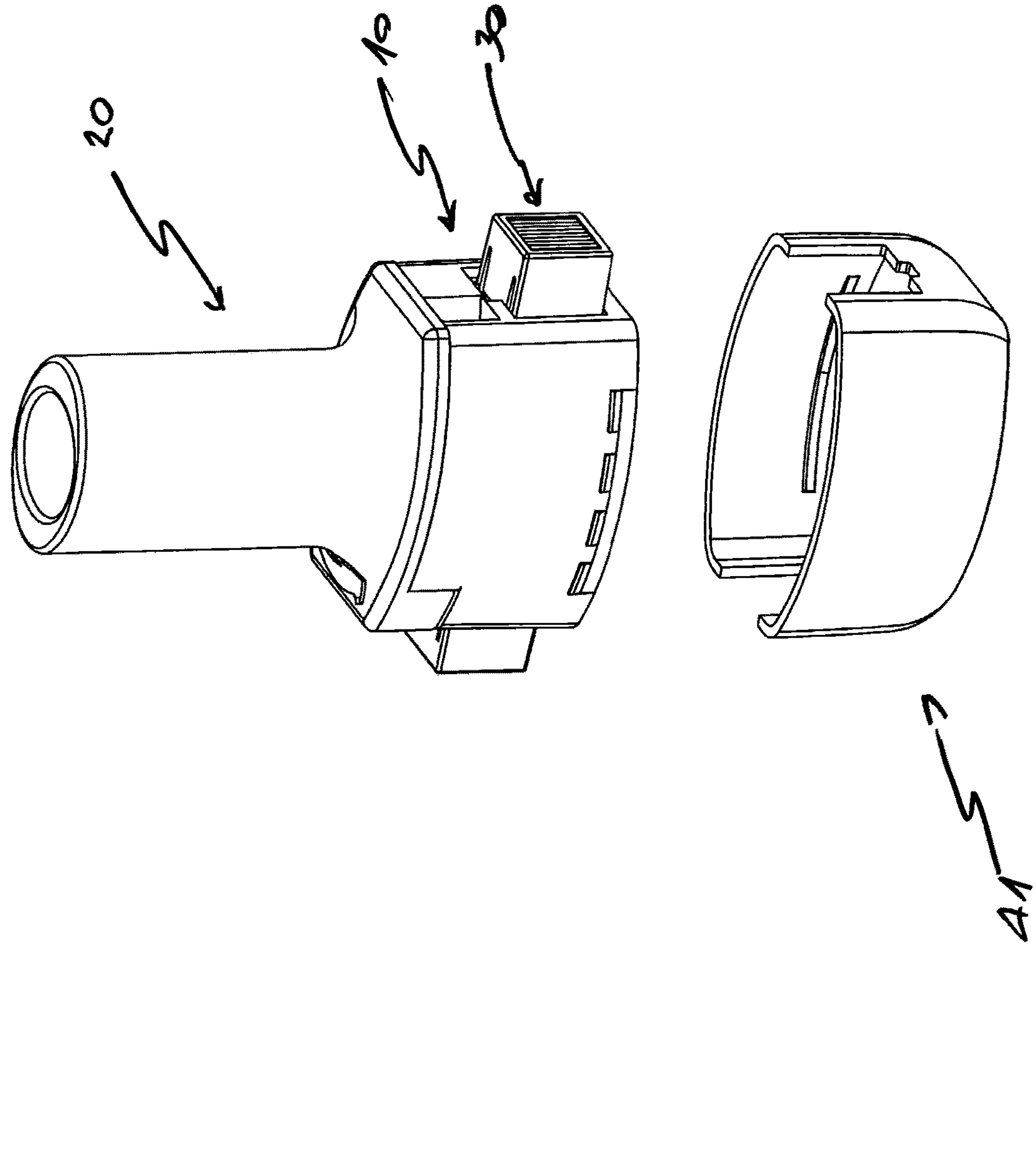
FIG. 11 illustrates a prospective view of an embodiment of an inhaler as disclosed herein.

The chamber may have an upper opening for inserting the capsule. The mouthpiece may be arranged to fit on top of the inhaler body in order to hold the capsule inside the chamber. In one embodiment, shown in FIG. 9, FIG. 10 and FIG. 11, the mouthpiece is detachably connectable to the inhaler body in order to be removed for inserting the capsule. Such mouthpiece is replaceable and may be selected according to the desired properties. In another embodiment, shown in FIG. 5, FIG. 6, FIG. 7 and FIG. 8, the mouthpiece is rotatably or slidably connected to the inhaler body in order to allow access to the chamber for inserting the capsule.

Figure 2:
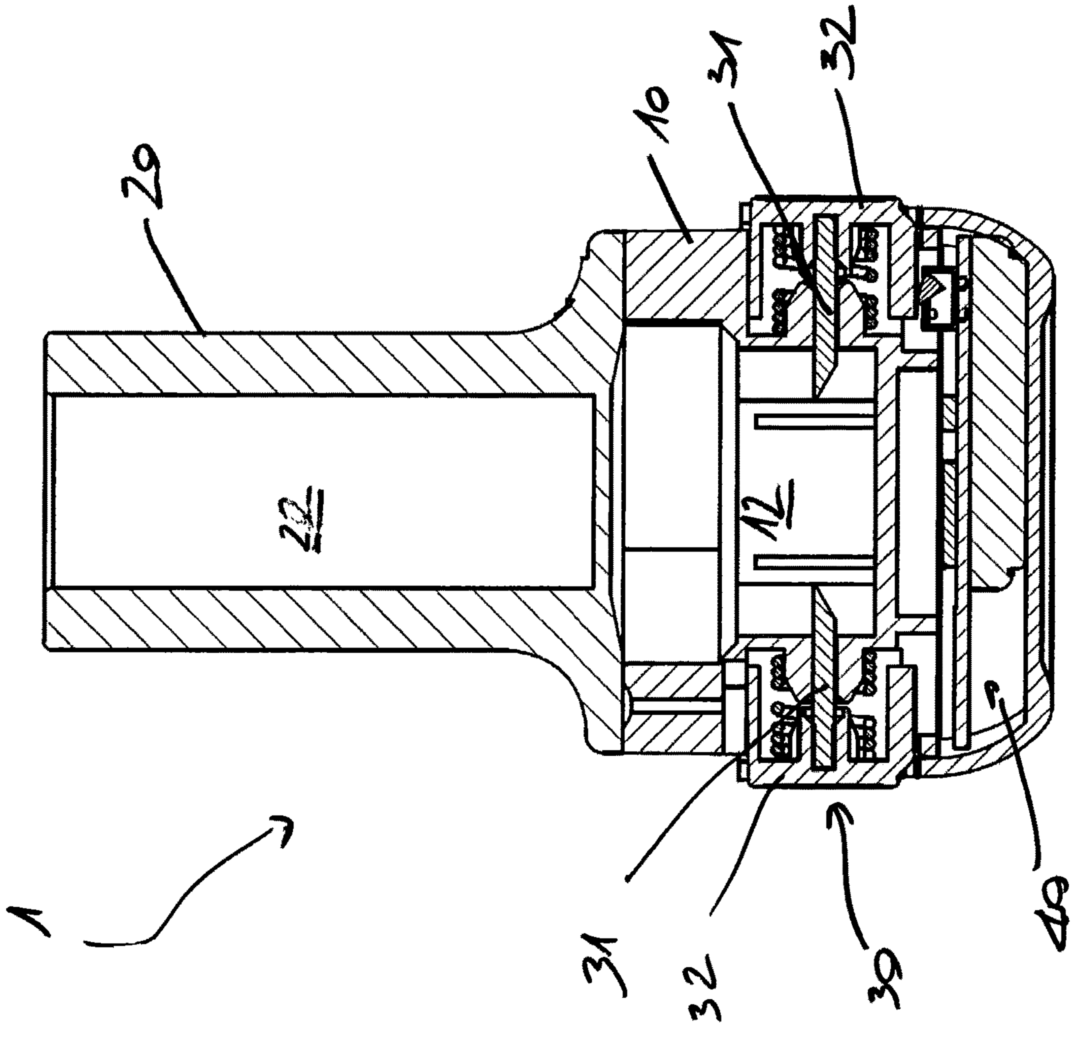
FIG. 2 illustrates a section view of the inhaler of FIG. 1 in a different operative condition.
Figure 3:
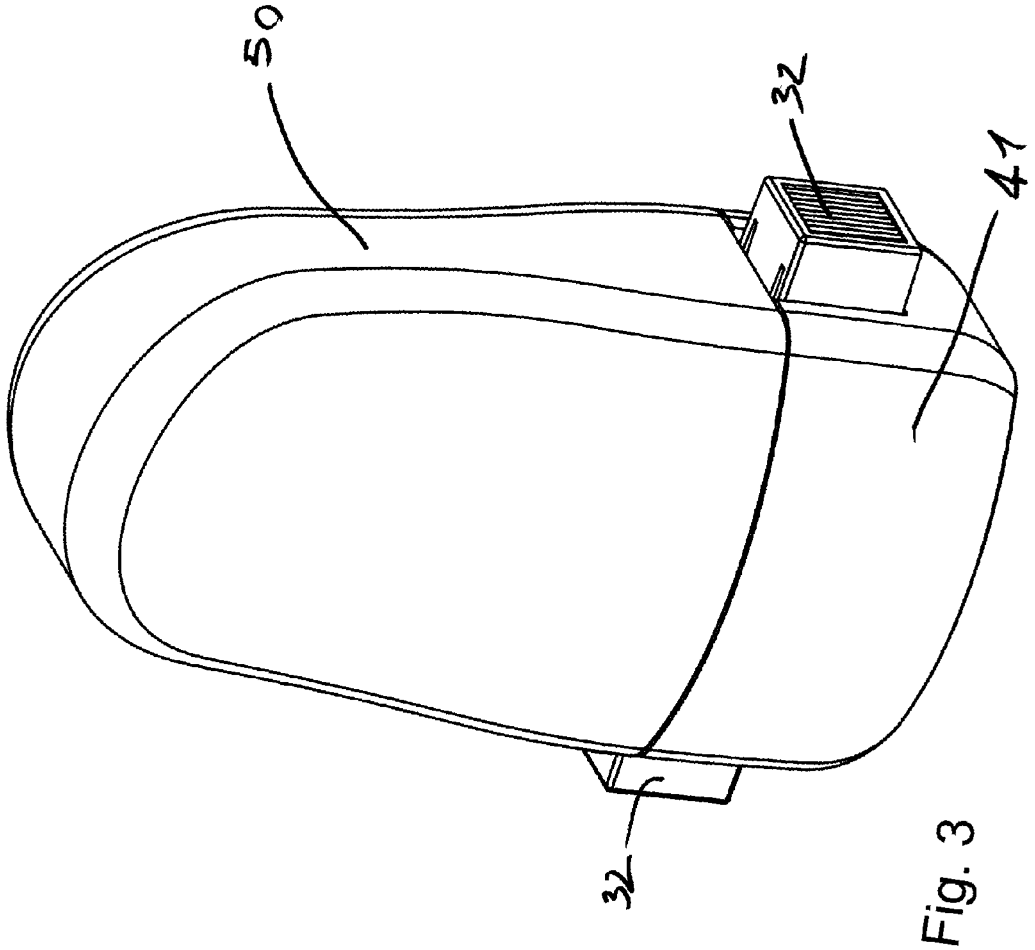
FIG. 3 illustrates a prospective view of an embodiment of an inhaler as disclosed herein.
Figure 4:
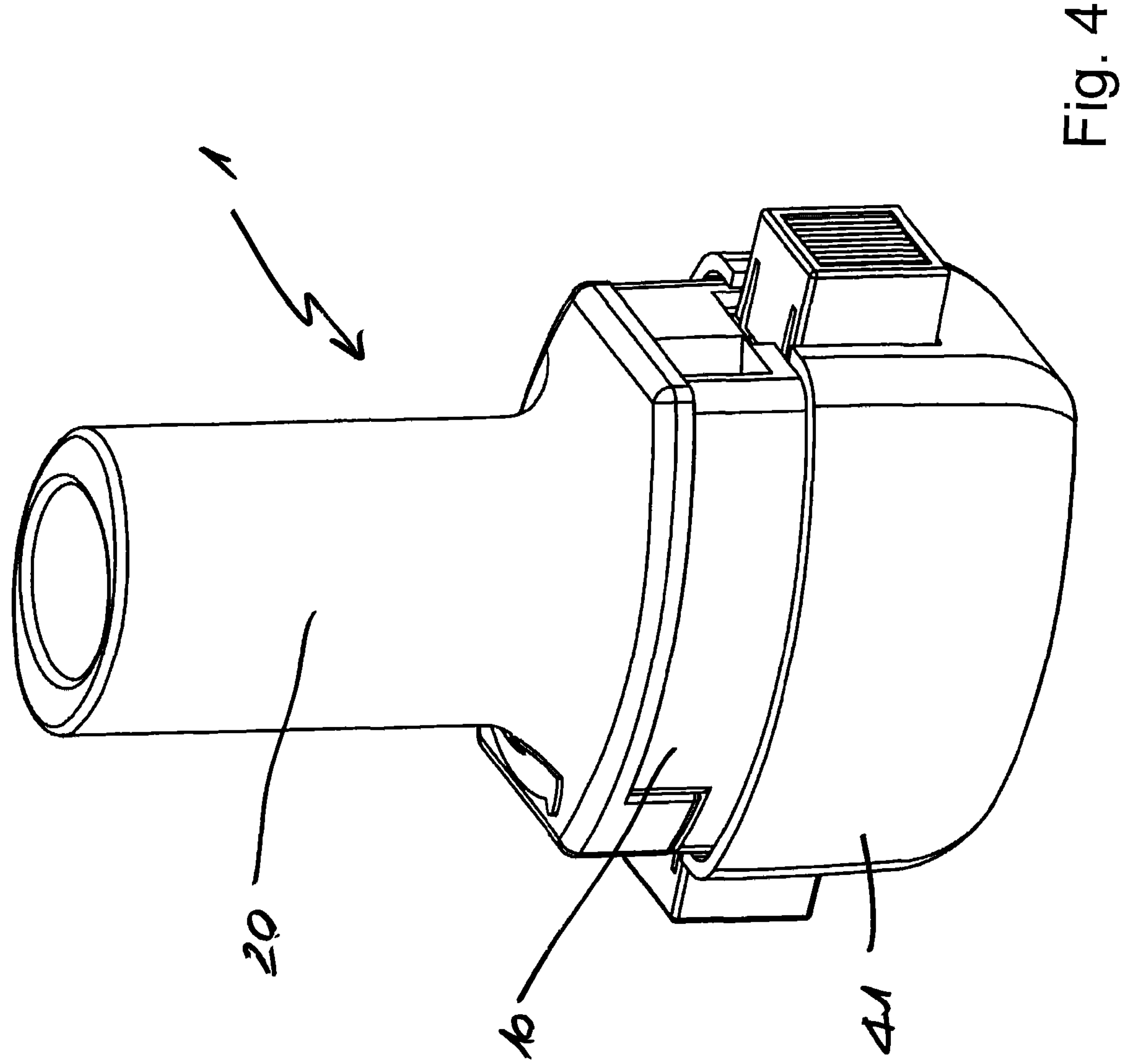
FIG. 4 illustrates a prospective view of an embodiment of an inhaler as disclosed herein.
Figure 5:
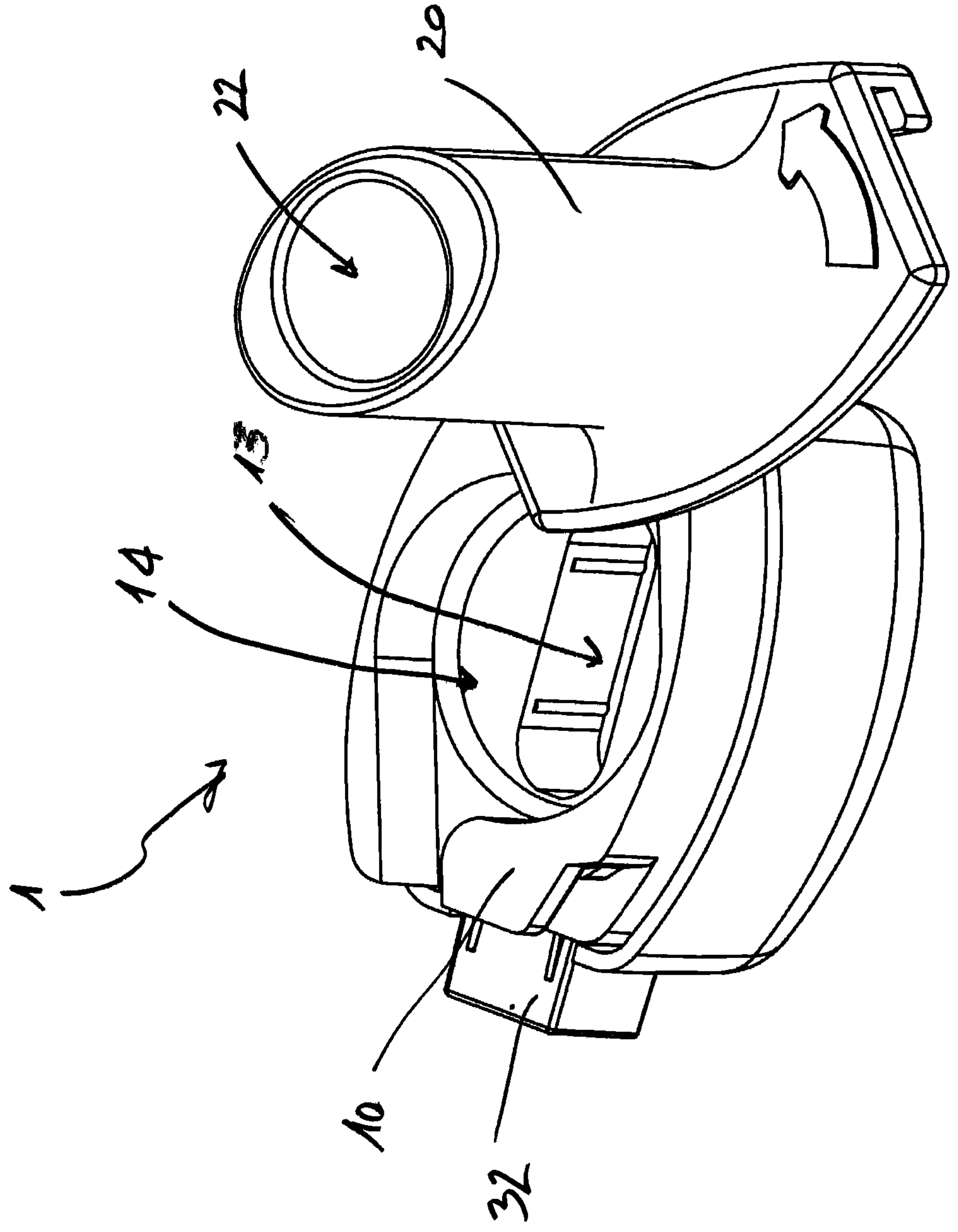
FIG. 5 illustrates a prospective view of the inhaler of FIG. 4 in a different operative condition.
Figure 6:
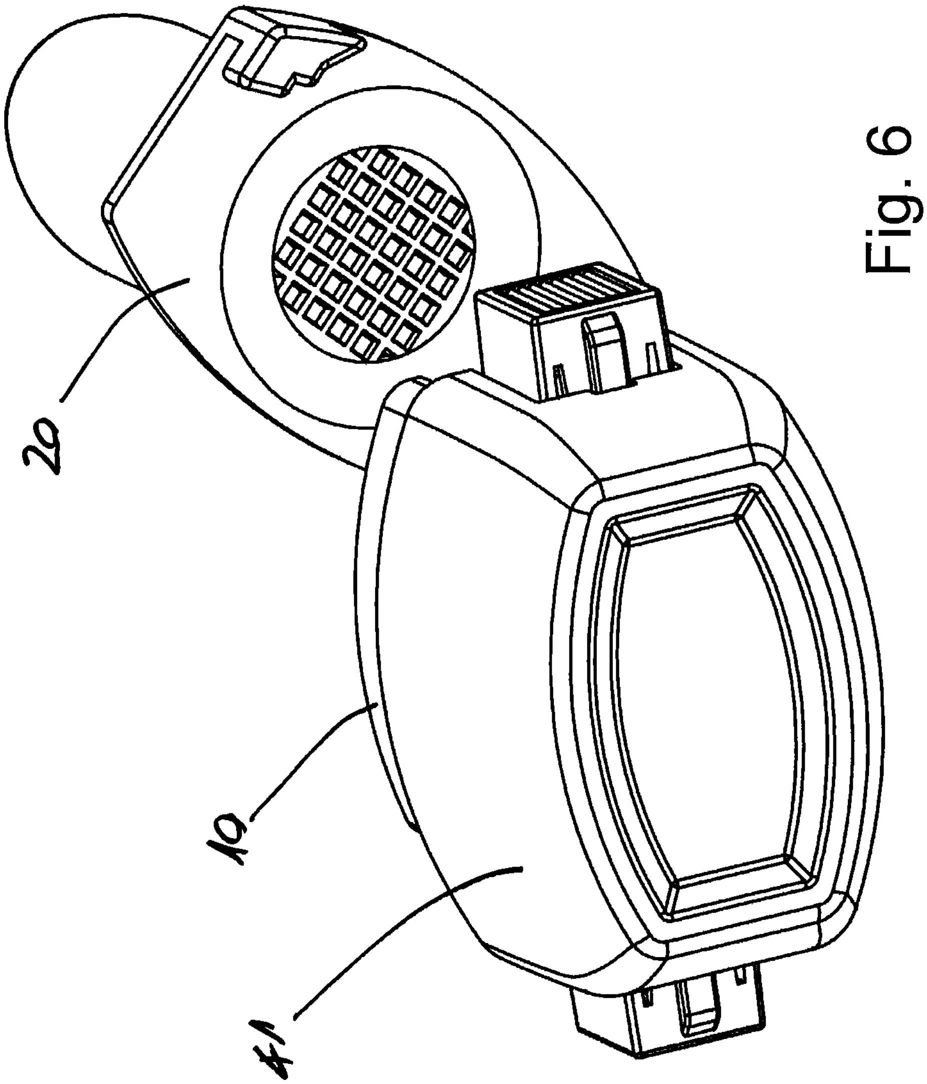
FIG. 6 illustrates a different prospective view of the inhaler of FIG. 5.
Figure 7:
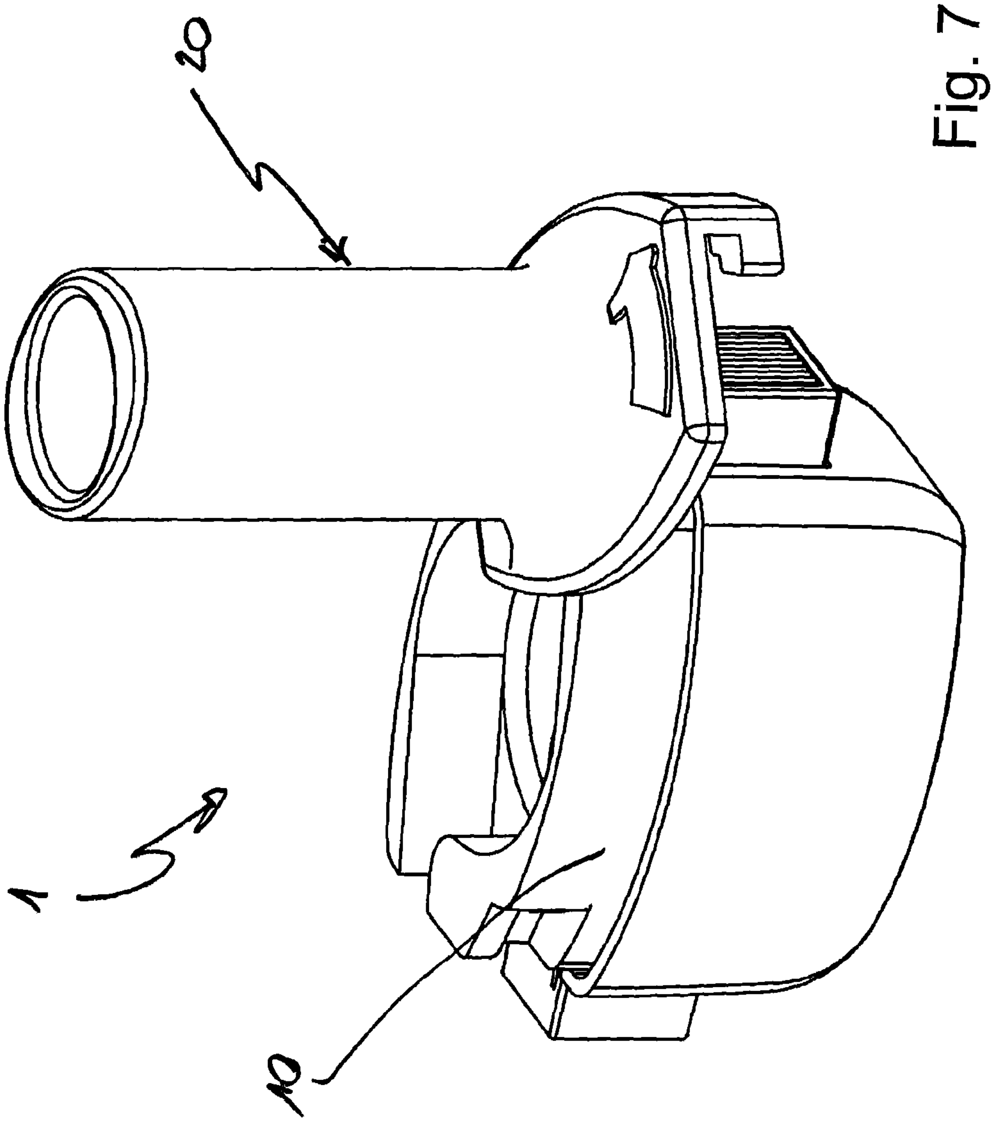
FIG. 7 illustrates a different prospective view of the inhaler of FIG. 5.
Figure 8:
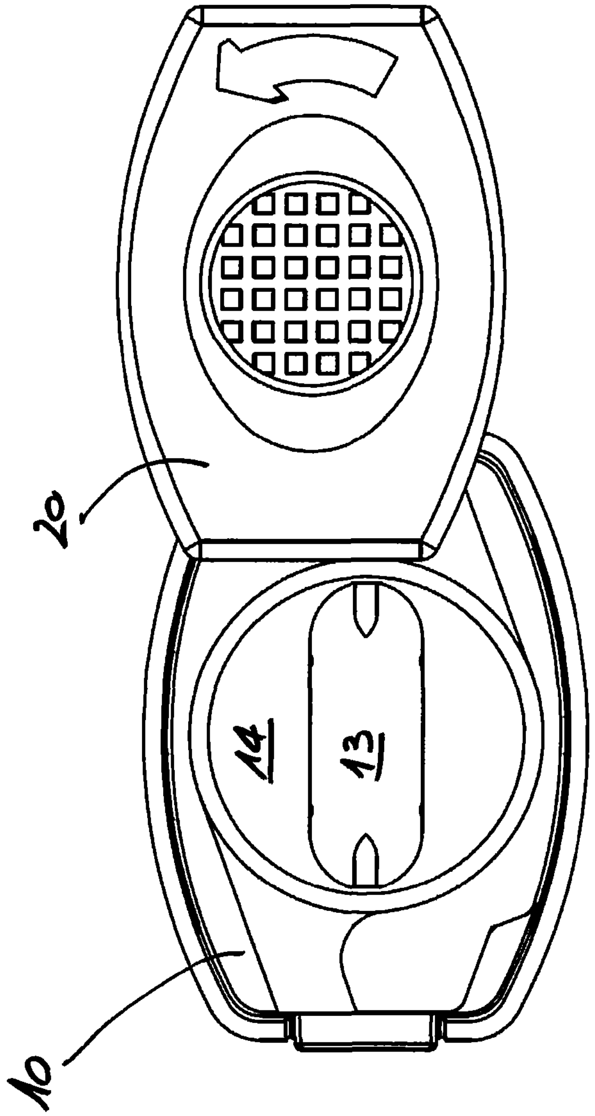
FIG. 8 illustrates a top view of an embodiment of an inhaler as disclosed herein.

The mouthpiece defines an inhalation channel (labeled 22 in the figures) in fluid communication with the chamber in order to allow an inhalation of a user through a free extremity of the mouthpiece while holding the capsule inside the chamber. The inhaler according to the present invention (labeled 1 in the figures) also comprises a capsule-piercing mechanism (labeled 30 in the figures) arranged to pierce a capsule located in the chamber. Preferably, such capsule-piercing mechanism comprises two needles (labeled 31 in the figures) or sharp bodies located at opposite sides of the chamber and two buttons (labeled 32 in the figures) protruding externally from the inhaler body in order to allow an actuation of the two needles by a user. FIG. 1 and FIG. 2 show a possible arrangement of the capsule piercing mechanism before and during activation respectively.

Preferably, the chamber (labeled 12 in the figures) has a bottom recess (labeled 13 in the figures) shaped in order to hold the capsule next to the capsule-piercing mechanism during the piercing operation and an upper volume (labeled 14 in the figures) arranged to allow an agitated motion of the capsule during an inhalation by the user. The inhalation body may have intake ducts arranged to determine a turbulent flow of air through the chamber and the inhalation channel. Preferably, such turbulent flow lifts the capsule from the bottom recess to the upper volume and causes an agitated motion of the capsule in the upper volume. The agitated motion favors the release of powder from the pierced capsule during the inhalation into the air flow directed to the mouth of the user.

In a possible embodiment, not shown in the enclosed figures, the inhaler comprises an agitation body, in particular a small oscillating sphere, inserted in the inhalation channel in order to be agitated by the air flow directed to the mouth of the user. According to the teachings of US2018369513, a similar device may be arranged for promoting the formation of extra-fine aerosol particles.

Figure 12:
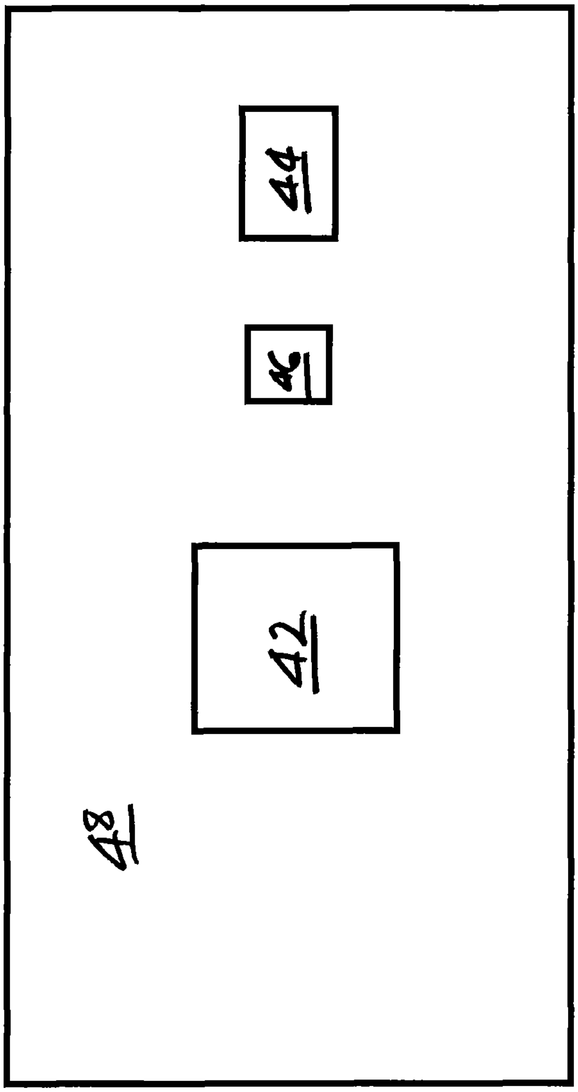
FIG. 12 illustrates a schematic view of a component of an inhaler as disclosed herein.

Advantageously, the inhaler according to the present invention (labeled 1 in the figures) comprises a monitoring system (labeled 40 in the figures) (see e.g. FIG. 12 but also FIG. 1 and FIG. 2) configured to monitor usage of the inhaler. According to possible embodiments, the monitoring system is integrated in the inhaler body. According to alternative embodiments, the monitoring system is integrated in a monitoring module that may be permanently or detachably attached to the inhaler body. Preferably, the inhaler is sealed in order to prevent contact of liquids with the monitoring system, which may occur for example during washing of the inhaler.

The monitoring system according to the present invention (labeled 40 in the figures) comprises an accelerometer (labeled 42 in the figures), which is preferably implemented as MEMS, in particular a 3-axis accelerometer possibly with an integrated temperature sensor such as LIS3DH manufactured by STMicroelectronics According to the present invention, an "accelerometer" is understood to be a sensor that translates (dynamic and static) accelerations of the sensor itself, that is designed to be mechanically coupled to a target object, into electronic signals. Advantageously, when coupled to a target object, the sensor can be used to measure its mechanical oscillations, and particularly the mechanical oscillations of the surface to which is directly coupled.

The accelerometer of the monitoring system according to the present invention is arranged to measure mechanical oscillations of the inhaler. In particular, the accelerometer is configured to detect and measure mechanical oscillations determined by the agitated motion of a capsule in the chamber and by air flow through the chamber and inhalation channel. The accelerometer is therefore able to measure the flow of the air independently from the agitated motion of the capsule. If the inhaler comprises an agitation body, the accelerometer may also be configured to detect and measure mechanical oscillations determined by the agitated motion of the agitation body. Preferably, the accelerometer has a sampling frequency equal or lower than 2 kHz, in order to accurately process frequencies in a band of interest between 100 Hz and 1 kHz, preferably between 200 Hz and 900 Hz. Advantageously, this relatively low sampling frequency allows to reliably generate inhalation data while reducing processing and memory requirements and optimizing system power consumption and cost.

There are prior-art solutions that use an acoustic sensor to monitor sound pressure indicative of an inhalation. A solution of this type is known from e.g. WO 2018/160073 A1.

Despite common confusion, acceleration sensors and acoustic sensors differ quite significantly. Accelerometers respond to accelerations, whereas microphones respond to pressure variations resulting from particles vibrating in the air and gas pressure waves in the air.

Such prior-art solutions are prone to suffer from signal disturbances, interference and errors caused by ambient noise sources present in the environment where the inhaler is used and monitored.

Advantageously, the accelerometer of the monitoring system according to the present invention is set up to measure not only the above-mentioned mechanical oscillations, but also parameters relating to other forces acting on the inhaler such as the orientation of the inhaler (thanks to a measurement of the direction of gravity) or accidental impacts which may result in damages to the inhaler.

The monitoring system according to the present invention (labeled 40 in the figures) may further comprise a detection unit (labeled 44 in the figures) arranged to detect an activation of a capsule-piercing mechanism (labeled 30 in the figures). According to an embodiment the detection unit comprises a mechanical switch, which the capsule-piercing mechanism is configured to engage upon activation. According to a different embodiment the detection unit comprises an optical switch and the capsule-piercing mechanism is configured to interfere with a transmission path of optical signals it generates. According to another different embodiment the detection unit comprises a magnetic switch and the capsule-piercing mechanism is configured to generate magnetic fields read by the magnetic switch upon activation.

The monitoring system according to the present invention (labeled 40 in the figures) may further comprise an electronic processing unit (labeled 46 in the figures) configured to receive signals from the accelerometer and from the detection unit. Reception of a signal from the detection unit triggers processing of signals from the accelerometer by the electronic processing unit in order to generate inhalation data. In particular, reception of a signal from the detection unit triggers processing of signals from the accelerometer by the electronic processing unit. In one embodiment, the accelerometer and the electronic processing unit are kept in a sleeping or low power mode and are woken up by a signal from the detection unit indicating activation of the capsule-piercing mechanism by a user. Advantageously, the detection unit allows an optimization in the processing of signals and in the battery consumption.

Preferably, the monitoring system according to the present invention (labeled 40 in the figures) comprises a transmitter-receiver unit, not shown in the attached figures, coupled with the electronic processing unit and configured to implement at least one radio communication with external electronic apparatus, for example a smartphone or a remote server. Such radio communication uses a standard from the short range related protocols communicating over a WPAN (including BLE, Bluetooth 5 and, IEEE 802.15.4, and all their variants) and a WLAN (including IEEE 802.11 and all their variants) or a direct internet connection using long range related protocols (including LoRaWAN, SigFox, EC-GSM, LTE, NB-IoT, LTE-M, and all their variants) without the need of an internet gateway. The transmitter-receiver unit may be configured to wirelessly exchange one or more of the following data:

- data relative to the conditions of the inhaler 1;
- data relative to properties of the inhaler body 10 and/or its model identifier;
- data relative to properties mouthpiece 20 and/or its model identifier;
- data relative to the capsule;
- data relative to inhalation(s);
- data relative to configurations of the monitoring system 40;
- data relative to a connection between the monitoring system 40 and external electronic apparatus.

Preferably, the monitoring system according to the present invention (labeled 40 in the figures) further comprises a printed circuit board (labeled 48 in the figures), mechanically coupled to the inhaler body in order to be affected, preferably directly, by the mechanical oscillations during inhalation by a user. According to one embodiment, the accelerometer, the detection unit and the electronic processing unit are soldered on the same printed circuit board; however, more printed circuit board may be provided. In particular, the printed circuit board is arranged to transmit the mechanical oscillations from the inhaler body to the accelerometer.

Typically, the mechanical coupling between the inhaler body and the printed circuit board allows mechanical oscillations to propagate without (significant) distortions and/or (significant) attenuations from the inhaler body to the printed circuit board. Such mechanical coupling may be rigid and/or elastic; for example, it may be rigid in some places and elastic in other places.

In some embodiments, the inhaler body, preferably its chamber, and/or the printed circuit board have at least one protrusion or additional rigid component for example for preloading the printed circuit board in order to optimize the transmission of mechanical oscillations to the printed circuit board; such additional rigid component may be (directly or indirectly) mechanically coupled with the printed circuit board and/or the inhaler body (preferably its chamber); such rigid component may be made of metal and may be advantageously soldered on the printed circuit board. It is to be noted that such rigid component may be coupled with the printed circuit board and/or the inhaler body (preferably its chamber) through an adhesive substance or adhesive element, hooks, clamps or snaps.

In some embodiments, the inhaler body, preferably its chamber, and the printed circuit board have at least one contact area where they are adherent so that the printed circuit board responds to the mechanical oscillations that are transmitted by the inhaler body. The printed circuit board may be held in contact with the external surface of the chamber while being preloaded using an additional elastic element in the inhaler body, in order to optimize the transmission of mechanical oscillations to the printed circuit board.

In some embodiments, the inhaler body, preferably its chamber, is in rigid contact with at least one rigid element, such as a metal pin, which is in rigid contact with the printed circuit board, which is preloaded using an additional elastic element in the inhaler body, in order to optimize the transmission of mechanical oscillations to the printed circuit board.

Preferably, the printed circuit board has low inertia, for example has a mass of less than 15 g or even less than 10 g. For example, the printed circuit board may have a thickness comprised between 0.4 mm and 1.6 mm, more preferably 0.6 mm and 1.0 mm and even more preferably between 0.7 mm and 0.9 mm.

Preferably, the printed circuit board is constrained to a support of the inhaler body at a peripheral region of the printed circuit board, for example by rigid protrusions engaging an edge of the printed circuit board (i.e. the outer border of the peripheral region).

Below the printed circuit board (i.e. opposite to the chamber) the inhaler is arranged (in particular configured) so to allow mechanical oscillations of the printed circuit board. It is to be noted that in FIG. 1 and in FIG. 2, the lower surface of the printed circuit board 48 seems in direct contact with a battery; however, there are special electrical contact elements in-between (such as for example Keystone 112TR and 110TR) in order to avoid the impediment of mechanical oscillations in the printed circuit board.

In order to improve the measurement of the mechanical oscillations most relevant to generate inhalation data, the accelerometer may be placed in a specific area of the board as identified by finite element method simulations, in particular in a central region of the printed circuit board and/or axially aligned with the chamber at a distance thereof.

One or more transmission elements (labeled 49*a* in the figures) may be interposed between the inhaler body and the printed circuit board, abutting against e.g. an inner border of the peripheral region of the printed circuit board. The transmission elements may be protrusions or rigid components, for example rigid and elongated pins protruding from a base of the inhaler body preferably from its chamber.

Above the printed circuit board (i.e. toward the chamber) the inhaler is arranged (in particular configured) so to allow mechanical oscillations of the printed circuit board. It is to be noted that the transmission elements (labeled 49*a* in the figures), if present, do not impede oscillations.

Preferably, the printed circuit board and/or its coupling with the inhaler body is arranged to mechanically amplify mechanical oscillations coming from the inhaler body to the printed circuit board during inhalation in order to optimize measurements by the accelerometer. For example, the printed circuit board might be designed to resonate at a frequency within or close to the band of interest of the mechanical oscillations. In such solutions the printed circuit board may be connected to the inhaler body through an elastic coupling designed to mechanically amplify the mechanical oscillations.

Advantageously, the monitoring system, including all its components, is entirely located externally to the chamber and the inhalation channel in order to avoid disturbing the inhalation flow.

The electronic processing unit is configured to process the signals from the accelerometer and the detection unit in order to estimate or evaluate one or more parameters of interest. Such parameters may be: inhalation flow rate, inhalation volume, peak inhalation flow rate, inhalation duration and presence of a capsule in the chamber. Advantageously, those parameters may be estimated on the basis of signals from the accelerometer, which is configured to pick up mechanical oscillation originating typically from vortices in the air flow in the chamber and in the inhalation channel in addition to (and independently from) the oscillations originating from the agitated motion of the capsule in the chamber.

The electronic processing unit may be configured to estimate or evaluate the above-mentioned parameters also on the basis of mechanical and/or design properties of the inhaler. These may include properties of the inhaler body, of the mouthpiece, and of the printed circuit board, such as its geometry and/or arrangement. For example the specific amplification of mechanical oscillations or the specific configuration of the chamber and/or inhalation duct (which affects the air flow during inhalation) might be taken into consideration. These properties may be preemptively stored inside a memory coupled with the electronic processing unit or may be estimated by the electronic processing unit on the basis of the signals from the accelerometer. The latter solution is particularly advantageous when parts of the inhaler such as the inhaler body, the mouthpiece and/or the monitoring module are replaceable. The latter solution is also useful in identifying damages or consumption of parts of the inhaler. Furthermore, the electronic processing unit may be configured to estimate or evaluate the above-mentioned parameters also on the basis of the orientation of the inhaler. The orientation may be estimated on the basis of the signals from the accelerometer which may contain information about the relative direction of gravity.

The programmability properties of the monitoring system according to the present invention, in particular its electronic processing unit, may be useful for example for reconfiguring it for different inhaler medications and/or inhaler models.

In one embodiment, not shown in the enclosed figures, the inhaler has a distinct surface or magnetic feature identifying a model of the inhaler, or a model of the inhaler body and/or mouthpiece in case the latter is detachable. A surface feature may include a geometrical feature or a reflective property of the surface, such as its color or finishing. For example, one or more magnets may be placed on the inhaler body or a particular detail of the inhaler body may be shaped or finished or colored in a determined way depending on the model type. In such embodiment, the monitoring system may be arranged to detect the surface or magnetic feature, preferably upon activation of the capsule-piercing mechanism. For example, a dedicated proximity or magnetic sensor may be arranged to detect such feature. Alternatively, the detection unit may be used also for detecting such feature (which is arranged to be detected by the detection unit). The electronic processing unit may be configured to associate the detected surface or magnetic feature to mechanical and/or design properties of the inhaler for estimating or evaluating the above-mentioned parameters. For example, the electronic processing unit may associate the detected feature to a specific configuration of the chamber and/or inhalation duct which affects the air flow during inhalation and the consequent mechanical oscillations.

In one embodiment, the electronic processing unit is configured to identify one or more of the following conditions, depending on one or more of the above-mentioned parameters:

A dose of powder formulation has been correctly inhaled, which may be identified for example when one or more of the cited parameters fall between a first predetermined value and a second predetermined value.

An incorrect inhalation has occurred, which may be identified for example when one or more of the cited parameters fall below a third predetermined value or above fourth predetermined value.

No inhalation has occurred for example in a predetermined amount of time from capsule-piercing.

In one embodiment, the electronic processing unit is also configured to identify one or more of the following conditions:

The capsule-piercing mechanism has been activated.

The power source is nearly exhausted.

The monitoring system is malfunctioning.

A connection with an external electronic device

In general, the electronic processing unit may be configured to determine whether a dose is taken or not at a given time, according to a predetermined schedule.

In one embodiment, the inhaler comprises a signaling device arranged to provide visual and/or audio emission, for example a lighting system and/or a piezoelectric buzzer. The electronic processing unit may be configured to drive the signaling device depending on the above-mentioned conditions, in particular by triggering a different emission for each identified condition.

In one embodiment, the signal from the accelerometer and/or the detection unit are relayed by the electronic processing unit to external electronic apparatus, for example a smartphone or a remote server, in the form of data transmitted through the transmitter-receiver unit. In such case at least part of the processing described above is carried out by the external electronic apparatus.

In one embodiment, the inhaler has an identifier, for example a QR code, configured to be read by an external electronic apparatus, for example a smartphone, in order to extract information about mechanical and/or design properties of the inhaler or its parts in order for those properties to be used in the estimation of the parameters. For example, in the case of removable inhaler body and mouthpiece, the two parts may each have an identifier and the external electronic apparatus is configured to transmit the relevant properties to the electronic processing unit through the transmitter-receiver unit. The identifier might also be associated with a user in order to monitor their use of the inhaler. In a possible embodiment the information is sent back by the external electronic apparatus to the electronic processing unit through the transmitter-receiver unit in order to be used in the estimation or evaluation of the above-mentioned parameters.

In general, the identifier may be used for providing information about mechanical and/or design properties and/or manufacturing data, of the inhaler and/or the inhaler body and/or the mouthpiece and/or the inhaler medication.

According to another aspect, the subject matter disclosed herein relates to a dry powder inhalation kit for pulmonary or nasal delivery comprising a plurality of modules which may be selected and assembled in order to build a dry power inhaler according to the present invention, in particular of the type described above.

The kit comprises: an inhaler body (labeled 10 in the figures), a mouthpiece (labeled 20 in the figures) detachably connectable to the inhaler body, a monitoring module (labeled 41 in the figures) detachably connectable to the inhaler body and preferably a cap (labeled 50 in the figures) for protecting the mouthpiece.

The components of the kit may have various design properties, which may be taken into account by the monitoring system thanks to the solutions described above for detecting the mechanical and/or design properties, and may be assembled to obtain inhalers according to the present invention, in particular of the type described above.

The subject matter disclosed herein improves known capsule based inhalers in different ways.

Advantageously, the use of an accelerometer and an appropriate configuration is a low-cost, low-power and reliable way to measure different parameters relating to inhalation.

Inhalation data allows monitoring the user's inspiratory trends and promoting better adherence and correcting inhaler technique.

The invention claimed is:

1. A dry powder inhaler for pulmonary or nasal delivery comprising:

a chamber for housing therein a capsule containing a dry powder formulation;

an inhalation channel in fluid communication with said chamber; and an inhaler body defining at least partially said chamber, said chamber being adapted to provide an agitated motion of said capsule in said chamber during an inhalation of a user through said inhalation channel, said dry powder inhaler further comprising:

a capsule-piercing mechanism arranged to pierce said capsule in said chamber; and a monitoring system comprising:

an accelerometer arranged to measure mechanical oscillations determined at least by said agitated motion and by a flow of air through said chamber and/or inhalation channel;

a detection unit arranged to detect an activation of the capsule-piercing mechanism; and an electronic processing unit comprising a processor configured to receive signals from said detection unit and from said accelerometer, wherein reception of a signal from said detection unit triggers processing of signals from said accelerometer by said electronic processing unit in order to generate inhalation data;

wherein said monitoring system comprises a printed circuit board mechanically coupled to said inhaler body in order to be affected by mechanical oscillations during said inhalation, wherein the mechanical coupling between said inhaler body and said printed circuit board is at least partially rigid and at least partially elastic so that mechanical oscillations propagate from said inhaler body to said printed circuit board, wherein said accelerometer is fixed on said printed circuit board in order to measure said mechanical oscillations, wherein at least a portion of the inhaler body is above the printed circuit board and at least a portion of the inhaler body is below the printed circuit board such that said printed circuit board is adapted to transmit the mechanical oscillations from the inhaler body to the accelerometer; and wherein the mechanical coupling is adapted to mechanically amplify the mechanical oscillations from the inhaler body to the printed circuit board in order to optimize measurements by the accelerometer;

wherein the electronic processing unit is configured to process said signals in order to estimate or evaluate one or more of the following parameters on the basis of said mechanical oscillations and of mechanical and/or design properties of the inhaler:

inhalation flow rate;

inhalation volume;

peak inhalation flow rate;

inhalation duration;

presence of a capsule in the chamber;

wherein said electronic processing unit is configured to estimate or evaluate an orientation of the inhaler based on the signals received from the accelerometer; and wherein said electronic processing unit is configured to estimate or evaluate said one or more parameters also on the basis of said estimated or evaluated orientation from the accelerometer.

2. The inhaler of claim 1, wherein said electronic processing unit is arranged to process mechanical oscillations measured by said accelerometer in the range from 100 Hz to 1000 Hz in order to generate inhalation data.

3. The inhaler of claim 1, wherein said printed circuit board is constrained to said inhaler body at a peripheral region of the printed circuit board.

4. The inhaler of claim 1, wherein at least a portion of the inhaler body is positioned above said printed circuit board and at least a portion of the inhaler body is positioned below said printed circuit board so as to allow mechanical oscillations of the printed circuit board.

5. The inhaler of claim 1, wherein said inhaler body and/or said printed circuit board have at least one contact area or at least one protrusion or additional rigid and/or elastic component for preloading the printed circuit board in order to optimize the transmission of mechanical oscillations to the printed circuit board.

6. The inhaler of claim 1, wherein said printed circuit board and/or the coupling between said inhaler body and said printed circuit board is arranged to mechanically amplify mechanical oscillations transferred from said inhaler body to said printed circuit board.

7. The inhaler of claim 1, wherein said monitoring system is entirely located externally to said chamber and said inhalation channel.

8. The inhaler of claim 1, wherein the detection unit comprises:

a mechanical switch, wherein the capsule-piercing mechanism is configured to engage said mechanical switch upon activation; or an optical switch, wherein the capsule-piercing mechanism is configured to interfere with a transmission path of optical signals generated by said optical switch; or a magnetic switch, wherein the mechanism is configured to generate magnetic fields read by said magnetic switch upon activation.

9. The inhaler of claim 1, comprising an agitation body inserted in said chamber and/or in said inhalation channel, said agitation body being arranged to be agitated during said inhalation, said accelerometer being arranged to also measure mechanical oscillations caused by said agitation body.

10. The inhaler of claim 1, wherein said accelerometer has a sampling frequency lower than or equal to 2 kHz.

11. The inhaler of claim 1, wherein the electronic processing unit is configured to estimate or evaluate said mechanical and/or design properties based on signals from said accelerometer.

12. The inhaler of claim 1, comprising an inhaler body defining at least partially said chamber and a mouthpiece detachably connected to said inhaler body, said mechanical and/or design properties including properties of the inhaler body and properties of the mouthpiece.

13. The inhaler of claim 12, having a distinct surface or magnetic feature identifying a model of the inhaler or a model of the inhaler body or a model of the mouthpiece; wherein said monitoring system is arranged to detect said surface or magnetic feature; and wherein said electronic processing unit is configured to associate said surface or magnetic feature to mechanical and/or design properties of the inhaler for estimating or evaluating said one or more parameters.

14. The inhaler of claim 12, wherein said inhaler and/or said inhaler body and/or said mouthpiece has an identifier arranged to be read by an external electronic apparatus in order to extract information about mechanical and/or design properties and/or manufacturing data of said inhaler and/or said inhaler body and/or said mouthpiece and/or inhaler medication.

15. The inhaler of claim 1, wherein said mechanical and/or design properties include a geometry and/or arrangement of said printed circuit board.

16. The inhaler of claim 1, wherein the electronic processing unit is configured to identify one or more conditions depending on said one or more parameters.

17. The inhaler of claim 16, comprising a signaling device arranged to provide visual and/or audio emission, wherein the electronic processing unit is configured to drive said signaling device depending on one or more of the identified conditions, in particular by triggering a different emission for each identified condition.

18. The inhaler of claim 1, comprising an inhaler body defining at least partially said chamber and a monitoring module detachably connected to said inhaler body, said monitoring module integrating said monitoring system.

19. A dry powder inhalation kit for pulmonary or nasal delivery, comprising:

an inhaler body;

a mouthpiece detachably connectable to said inhaler body;

a monitoring module detachably connectable to the inhaler body, said inhaler body and said mouthpiece defining, when connected, a chamber for housing therein a capsule containing a dry powder formulation and an inhalation channel in fluid communication with said chamber, said chamber being adapted to provide an agitated motion of said capsule in said chamber during an inhalation of a user through said inhalation channel; and a capsule-piercing mechanism arranged on said inhaler body to pierce said capsule in said chamber;

said monitoring module integrating a monitoring system comprising:

an accelerometer arranged on a printed circuit board in order to be affected by mechanical oscillations during said inhalation and to measure the mechanical oscillations determined at least by said agitated motion and by a flow of air through said chamber and/or inhalation channel;

a detection unit arranged to detect an activation of the capsule-piercing mechanism; and an electronic processing unit comprising a processor configured to receive signals from said detection unit and from said accelerometer, wherein reception of a signal from said detection unit triggers processing of signals from said accelerometer by said electronic processing unit in order to generate inhalation data;

further including a mechanical coupling between the printed circuit board and the monitoring module that is at least partially rigid and at least partially elastic so that mechanical oscillations propagate from the inhaler body, through the monitoring module, to the printed circuit board;

wherein at least a portion of the monitoring module is above the printed circuit board and at least a portion of the monitoring module is below the printed circuit board such that the printed circuit board is adapted to transmit the mechanical oscillations from the monitoring module to the accelerometer; and wherein the mechanical coupling is adapted to modify the mechanical oscillations from the inhaler body and transmitted via the monitoring module to the printed circuit board in order to optimize measurements by the accelerometer;

wherein the electronic processing unit is configured to process said signals in order to estimate or evaluate one or more of the following parameters on the basis of said mechanical oscillations and of mechanical and/or design properties of the inhaler:

inhalation flow rate;
inhalation volume;
peak inhalation flow rate;
inhalation duration;
presence of a capsule in the chamber;

wherein said electronic processing unit is configured to estimate or evaluate an orientation of the inhaler based on the signals received from the accelerometer; and wherein said electronic processing unit is configured to estimate or evaluate said one or more parameters also on the basis of said estimated or evaluated orientation from the accelerometer.

* * * * *